(12) United States Patent
Mapiye et al.

(10) Patent No.: US 12,093,803 B2
(45) Date of Patent: Sep. 17, 2024

(54) DOWNSAMPLING GENOMIC SEQUENCE DATA

(71) Applicant: International Business Machines Corporation, Armonk, NY (US)

(72) Inventors: Darlington Shingirirai Mapiye, Randburg (ZA); James Junior Mashiyane, Selcourt (ZA); Stephanie Julia Muller, Pretoria (ZA); Mpho Mokoatle, Orkney (ZA); Gciniwe Dlamini, Johannesburg (ZA)

(73) Assignee: International Business Machines Corporation, Armonk, NY (US)

( * ) Notice: Subject to any disclaimer, the term of this patent is extended or adjusted under 35 U.S.C. 154(b) by 797 days.

(21) Appl. No.: 16/918,012

(22) Filed: Jul. 1, 2020

(65) Prior Publication Data
US 2022/0004847 A1    Jan. 6, 2022

(51) Int. Cl.
*G06N 3/045*    (2023.01)
*G06N 3/088*    (2023.01)
(Continued)

(52) U.S. Cl.
CPC ............. *G06N 3/045* (2023.01); *G06N 3/088* (2013.01); *G16B 30/10* (2019.02); *G16B 40/30* (2019.02)

(58) Field of Classification Search
CPC ........ G06N 3/045; G06N 3/088; G16B 30/10; G16B 40/30
(Continued)

(56) References Cited

U.S. PATENT DOCUMENTS

| 6,760,668 | B1 |   | 7/2004 | Izmailov |   |
|---|---|---|---|---|---|
| 8,412,462 | B1 | * | 4/2013 | Ganeshalingam | G16B 20/00 |
|   |   |   |   |   | 702/19 |

(Continued)

FOREIGN PATENT DOCUMENTS

| CA | 3040138 A1 | 4/2018 |
| CN | 103559020 B | 7/2016 |

(Continued)

OTHER PUBLICATIONS

Absardi & Javidan, 2019, "A Fast Reference-Free Genome Compression Using Deep Neural Networks" (Year: 2019).*

(Continued)

*Primary Examiner* — Marc S Somers
*Assistant Examiner* — Jun Kwon
(74) *Attorney, Agent, or Firm* — Joseph P. Curcuru

(57) ABSTRACT

In an approach to automatically downsampling DNA sequence data using variational autoencoders and preserving genomic integrity of an original file embodiments execute, by an encoder, bootstrapping on genomic sequence data to produce resamples. Furthermore, embodiments assess, by the encoder, unrepresentativeness and self-inconsistency of the resamples and selecting a representative resample according to the assessment, and build, by a modified encoder, vector representations from genotype likelihoods based on the selected representative sample. Additionally, embodiments integrate, by an analytics engine, mapping positional information and the genotype likelihoods to identify an optimum vector representation of a resample, and decode, by a modified decoder, the identified optimum vector representation of the resample to obtain a downsampled read file that resembles and maintains the genomic integrity of the original file.

20 Claims, 6 Drawing Sheets

(51) Int. Cl.
*G16B 30/10* (2019.01)
*G16B 40/30* (2019.01)

(58) Field of Classification Search
USPC .......................................................... 706/22
See application file for complete search history.

(56) References Cited

U.S. PATENT DOCUMENTS

| | | | |
|---|---|---|---|
| 9,552,458 B2 | 1/2017 | White | |
| 10,354,747 B1 | 7/2019 | Depristo | |
| 2013/0246460 A1* | 9/2013 | Maltbie | G16B 50/40 707/771 |
| 2016/0306922 A1 | 10/2016 | Van Rooyen | |
| 2018/0052953 A1 | 2/2018 | Ganeshalingam | |
| 2018/0152535 A1* | 5/2018 | Sade | G16B 50/50 |
| 2019/0020353 A1 | 1/2019 | Erlich | |
| 2019/0244678 A1* | 8/2019 | Konvicka | G16B 30/00 |
| 2019/0330680 A1 | 10/2019 | Kennedy | |
| 2019/0348147 A1 | 11/2019 | Kaseniit | |
| 2020/0258597 A1* | 8/2020 | Perera | G16B 20/20 |
| 2021/0183472 A1* | 6/2021 | Barbour | G16B 40/20 |

FOREIGN PATENT DOCUMENTS

| | | | | |
|---|---|---|---|---|
| WO | WO-2019055835 A1 * | 3/2019 | | G16B 20/20 |
| WO | 2019169044 A1 | 9/2019 | | |
| WO | 2019170773 A1 | 9/2019 | | |

OTHER PUBLICATIONS

Mortier, 2016, "Non-reference-based DNA read compression using machine learning techniques" (Year: 2016).*

Asgari et al, 2018, "MicroPheno: predicting environments and host phenotypes from 16S rRNA gene sequencing using a k-mer based representation of shallow sub-samples" (Year: 2018).*

Cai et al, 2017, "ESPRIT-Forest: Parallel clustering of massive amplicon sequence data in subquadratic time" (Year: 2017).*

Aliferi et al, 2018, "DNA methylation-based age prediction using massively parallel sequencing data and multiple machine learning models" (Year: 2018).*

Wang & Gu, 2018, "VASC: Dimension Reduction and Visualization of Single-cell RNA-seq Data by Deep Variational Autoencoder" (Year: 2018).*

Nicolae, 2015, "LFQC: a lossless compression algorithm for FASTQ files" (Year: 2015).*

Voges et al, 2018, "CALQ: compression of quality values of aligned sequencing data" (Year: 2018).*

Friedensohn et al, Feb. 2020, "Convergent selection in antibody repertoires is revealed by deep learning" (Year: 2020).*

Greenfield et al, 2016, "GeneCodeq: quality score compression and improved genotyping using a Bayesian framework" (Year: 2016).*

Janin et al, 2014, "BEETL-fastq: a searchable compressed archive for DNA reads" (Year: 2014).*

Yang et al, 2019, "SQUAT: a Sequencing Quality Assessment Tool for data quality assessments of genome assemblies" (Year: 2019).*

"Patent Cooperation Treaty PCT International Search Report", International application No. PCT/IB2021/055058, International filing date Jun. 9, 2021, date of mailing Sep. 13, 2021, 8 pages.

Amaral et al, "Application of massive parallel sequencing to whole genome SNP discovery in the porcine genome", BMC Genomics Bio Med Central, Published: Aug. 12, 2009, BMC Genomics 2009, doi:10.1186/1471-2164-10-374, 10 pages.

Asgari et al., "MicroPheno: predicting environments and host phenotypes from 16S rRNA gene sequencing using a k-mer based representation of shallow sub-samples", Oxford, Bioinformatics, 34, 2018, i32-i42, doi: 10.1093/bioinformatics/bty296, ISMB 2018, 11 pages.

Deorowicz et al., "Compression of DNA sequence reads in FASTQ format", Bioinformatics, Applications Note, vol. 27 No. 6 2011, pp. 860-862 doi: 10.1093/bioinformatics/btr014, Advance Access publication Jan. 19, 2011, 3 pages.

Rideout et al., "Subsampled open-reference clustering creates consistent, comprehensive OTU definitions and scales to billions of sequences", PeerJ, Published Aug. 21, 2014, © Copyright 2014 Rideout, 25 pages.

Rieber et al., "Coverage Bias and Sensitivity of Variant Calling for Four Whole-genome Sequencing Technologies", PLOS | ONE, Jun. 2013 | vol. 8 | Issue 6 | e66621, 11 pages.

Sedlar et al., "Prokaryotic DNA Signal Downsampling for Fast Whole Genome Comparison", ResearchGate, Chapter—May 2014, DOI: 10.1007/978-3-319-06593-9_33, 12 pages, <https://www.researchgate.net/publication/265058445_Prokaryotic_DNA_Signal_Downsampling_for_Fast_Whole_Genome_Comparison>.

Sinai et al., "Variational auto-encoding of protein sequences", arXiv:1712.03346v3 [q-bio.QM] Jan. 3, 2018, 6 pages.

Yanovsky, Vladimir, "ReCoil—an algorithm for compression of extremely large datasets of DNA data", Yanovsky Algorithms for Molecular Biology 2011, 6:23, http://www.almob.org/content/6/1/23, AMG Algorithms for Molecular Biology, 9 pages.

Zheng et al., "Parallel Compression and Decompression of DNA Sequence Reads in FASTQ Format", International Journal of Hybrid Information Technology vol. 7, No. 4 (2014), pp. 91-100, http://dx.doi.org/10.14257/ijhit.2014.7.4.09, 10 pages.

* cited by examiner

DOWNSAMPLING GENOMIC SEQUENCE DATA

BACKGROUND OF THE INVENTION

The present invention relates generally to the field of genomic sequence data, and more particularly to downsampling deoxyribonucleic acid (DNA) sequence data.

Genomes are sequenced every day, wherein a single human genome may take up to 100 gigabytes of storage space, thus, storage needs for genomic sequence data will grow from gigabytes to petabytes to exabytes. Moreover, for every 3 billion bases of the human genome sequence, a 30-fold increase in data (approximately 100 gigabases) must be collected because of errors in sequencing, base calling, and genome alignment. This means that as much as 2-40 exabytes of storage capacity will be needed by the year 2025 just for the human genomes. In digital signal processing, downsampling, compression, and decimation are terms associated with the process of resampling in a multi-rate digital signal processing system. Both downsampling and decimation can be synonymous with compression, or they can describe an entire process of bandwidth reduction (filtering) and sample-rate reduction. When the process is performed on a sequence of samples of a particular signal or other continuous functions, downsampling produces an approximation of the sequence that would have been obtained by sampling the signal at a lower rate (or density, as in the case of a photograph).

The advent of massively parallel high-throughput sequencing technology known as next generation sequencing (NGS) has revolutionized the field of biological sciences. The advent of NGS has led to an increase in the amount and availability of DNA sequence data. The ultra-high scale and efficient NGS sequencing machines can produce billions of short DNA reads in excess of a few terabytes of data in a single run. The short DNA reads are stored in FASTQ files (plain text files in gigabytes), which are used for a wide range of applications such as gene annotations, expression studies, personalized treatment and precision medicine, wherein a FASTQ file is a file in FASTQ format. FASTQ format is a text-based format for storing both a biological sequence (usually nucleotide sequence) and its corresponding quality scores. Both the sequence letter and quality score are each encoded with a single American Standard Code for Information Interchange (ASCII) character for brevity.

SUMMARY

Embodiments of the present invention disclose a method, a computer program product, and a system for automatically downsampling DNA sequence data using variational autoencoders and preserving genomic integrity of an original file, the method comprising: executing, by an encoder, bootstrapping on genomic sequence data to produce resamples; assessing, by the encoder, unrepresentativeness and self-inconsistency of the resamples and selecting a representative resample according to the assessment; building, by a modified encoder, vector representations from genotype likelihoods based on the selected representative sample; integrating, by an analytics engine, mapping positional information and the genotype likelihoods to identify an optimum vector representation of a resample; and decoding, by a modified decoder, the identified optimum vector representation of the resample to obtain a down-sampled read file that resembles and maintains the genomic integrity of the original file.

DETAILED DESCRIPTION

Figure 1:
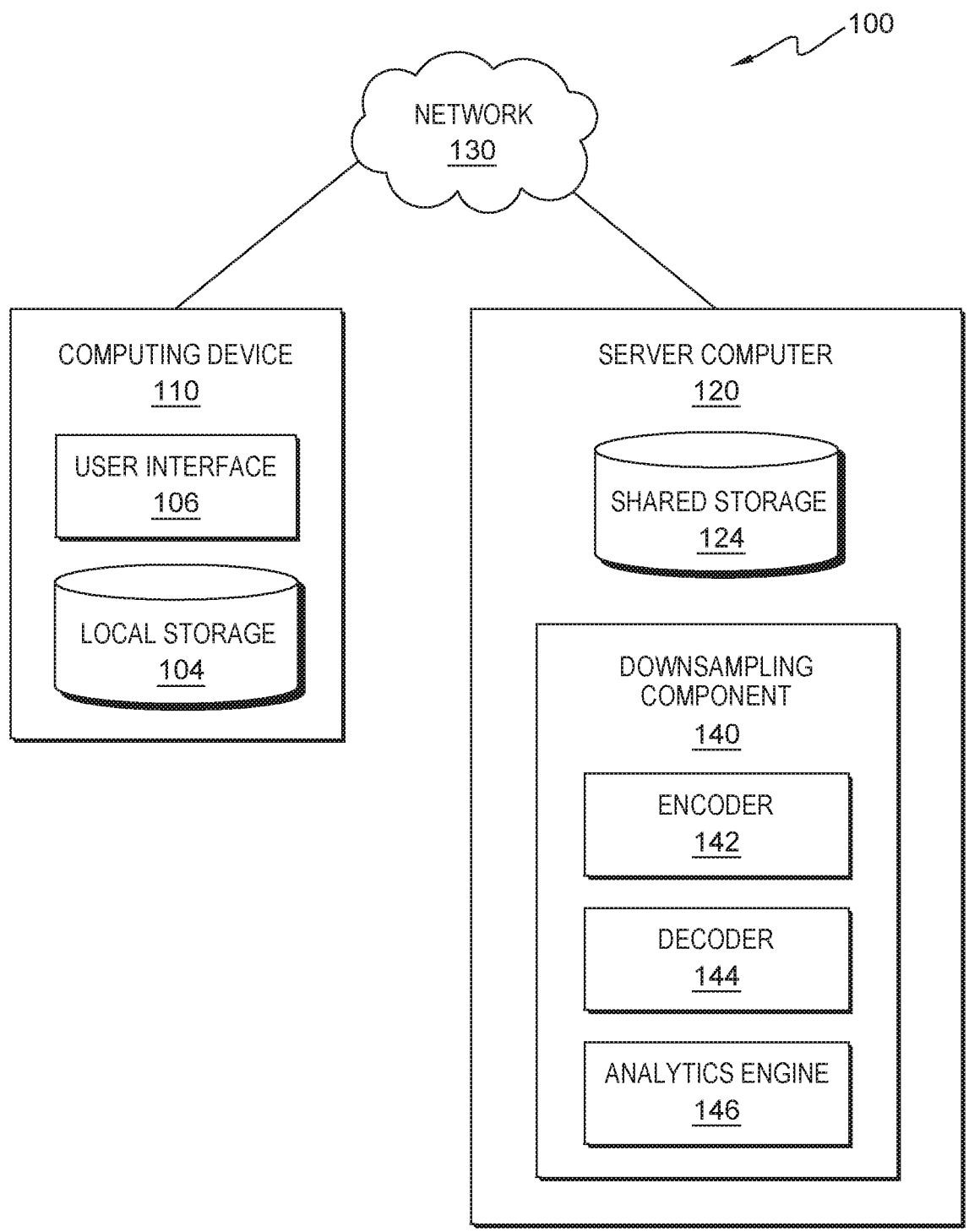
FIG. 1 is a functional block diagram illustrating a distributed data processing environment, in accordance with an embodiment of the present invention.

Embodiments of the present invention recognize that there are issues with the current methods and systems for genomic data analysis and integrating and archiving DNA sequence data. For example, the high-throughput genome sequencing inherently produces files containing millions of reads per sample, files requiring large computing resources for storage and processing, and samples that need to be effectively summarized (e.g. downsampling) to optimize computational efficiency. Embodiments of the present invention recognize that current methods of downsampling do not maintain the genomic integrity of the original sample.

It is known in the art that the surge of genomic data poses huge challenges in analyzing, integrating, sharing and archiving DNA sequence data. Embodiments of the present invention solve the problems stated above by presenting a system and method for down-sampling billions of reads in a FASTQ file to reduce the file size and amount of DNA reads while preserving the integrity of the original information and avoiding loss of important genomic information, wherein the loss of information is mainly attributed to the loss of genomic variation such as structural variation that is encode in a plethora of reads, thus, enabling more effective and efficient downstream processing and analysis of genomic sequence data.

Additionally, embodiments of the present invention summarize genomic information using a composite representation. Embodiments of the present invention take into account the genome sequence data as a whole and transform the genomic information (e.g., the genome sequence data as a whole) into a representation (e.g., numerical vector) that keeps the original biological information intact, wherein the input data is from DNA sequencing for multiple reads (e.g., analyzes, identifies, and/or interprets transformations for a plurality of reads). In various embodiments of the present invention, the biological information that is mostly capture and encoded into reads are the different types of variations known in the art, such as insertion-deletion mutations (indels), single-nucleotide polymorphisms (SNPs), and/or code-number variations (cnvs) that can be used to explain different phenotypes. Furthermore, embodiments of the present invention utilize shallow sampling using a bootstrapping approach to calculate a minimum value of representativeness and consistence. In some embodiments of the present invention, the present invention is not focused on single-nucleotide polymorphism (SNP) calling, but rather genotype likelihood estimation at multiple positions within a read. Embodiments of the present invention may use a graphical Poisson distribution to estimate genotype likelihoods. In various embodiments of the present invention, the present invention is a downsampling method and, in some instances, is alignment free. Embodiments of the present invention recognize that an alignment works when a user (i.e., researcher) possesses a reference genome and in most cases the reference genome is incomplete resulting in the alignment being dependent on the reference genome (i.e., the alignment is only as good as your reference). In various embodiments of the present invention, the present invention is focused on genotype likelihood estimation at multiple positions within a read to use as prior information without relying on variant calling techniques.

Implementation of embodiments of the invention may take a variety of forms, and exemplary implementation details are discussed subsequently with reference to the Figures (i.e., FIG. 1-FIG. 4).

FIG. 1 is a functional block diagram illustrating a distributed data processing environment, generally designated 100, in accordance with one embodiment of the present invention. The term "distributed" as used in this specification describes a computer system that includes multiple, physically distinct devices that operate together as a single computer system. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims. Distributed data processing environment 100 includes computing device 110 and server computer 120 interconnected over network 130.

Network 130 may be, for example, a storage area network (SAN), a telecommunications network, a local area network (LAN), a wide area network (WAN), such as the Internet, a wireless technology for exchanging data over short distances (using short-wavelength ultra-high frequency (UHF) radio waves in the industrial, scientific and medical (ISM) band from 2.4 to 2.485 GHz from fixed and mobile devices, and building personal area networks (PANs) or a combination of the three), and may include wired, wireless, or fiber optic connections. Network 130 may include one or more wired and/or wireless networks that may receive and transmit data, voice, and/or video signals, including multimedia signals that include voice, data, text and/or video data. In general, network 130 may be any combination of connections and protocols that will support communications between computing device 110 and server computer 120, and any other computing devices and/or storage devices (not shown in FIG. 1) within distributed data processing environment 100.

In some embodiments of the present invention, computing device 110 may be, but is not limited to, a standalone device, a client, a server, a laptop computer, a tablet computer, a netbook computer, a personal computer (PC), a smart phone, a desktop computer, a smart television, a smart watch, a radio, a stereo system, a cloud based service (e.g., a cognitive cloud based service), AR glasses, a virtual reality headset, any HUD known in the art, and/or any programmable electronic computing device capable of communicating with various components and devices within distributed data processing environment 100, via network 130 or any combination therein. In general, computing device 110 may be representative of any programmable computing device or a combination of programmable computing devices capable of executing machine-readable program instructions and communicating with users of other computing devices via network 130 and/or capable of executing machine-readable program instructions and communicating with server computer 120. In some embodiments computing device 110 may represent a plurality of computing devices.

In some embodiments of the present invention, computing device 110 may represent any programmable electronic computing device or combination of programmable electronic computing devices capable of executing machine readable program instructions, manipulating executable machine-readable instructions, and communicating with server computer 120 and other computing devices (not shown) within distributed data processing environment 100 via a network, such as network 130. Computing device 110 may include an instance of user interface (interface) 106, and local storage 104. In various embodiments, not depicted in FIG. 1, computing device 110 may have a plurality of user interfaces. In other embodiments, not depicted in FIG. 1, distributed data processing environment 100 may comprise a plurality of computing devices, plurality of server computers, and/or one a plurality of networks. Computing device 110 may include internal and external hardware components, as depicted, and described in further detail with respect to FIG. 4.

User interface (interface) 106 provides an interface to predictive component 140. Computing device 110, via user interface 106, may enable a user and/or a client to interact with component 140 and/or server computer 120 in various ways, such as sending program instructions, receiving program instructions, sending and/or receiving messages, updating data, sending data, inputting data, editing data, collecting data, and/or receiving data. In one embodiment, interface 106 may be a graphical user interface (GUI) or a web user interface (WUI) and may display at least text, documents, web browser windows, user options, application interfaces, and instructions for operation. interface 106 may include data (such as graphic, text, and sound) presented to a user and control sequences the user employs to control operations. In another embodiment, interface 106 may be a mobile application software providing an interface between a user of computing device 110 and server computer 120. Mobile application software, or an "app," may be designed to run on smart phones, tablet computers and other computing devices. In an embodiment, interface 106 may enable the user of computing device 110 to at least send data, input data, edit data (annotations), collect data and/or receive data.

Server computer 120 may be a standalone computing device, a management server, a web server, a mobile computing device, one or more client servers, or any other electronic device or computing system capable of receiving, sending, and processing data. In other embodiments, server computer 120 may represent a server computing system utilizing multiple computers such as, but not limited to, a server system, such as in a cloud computing environment. In another embodiment, server computer 120 may represent a computing system utilizing clustered computers and components (e.g., database server computers, application server computers, etc.) that act as a single pool of seamless resources when accessed within distributed data processing environment 100. Server computer 120 may include internal and external hardware components, as depicted, and described in further detail with respect to FIG. 4. In some embodiments server computer 120 may represent a plurality of server computers.

Each of shared storage 124 and local storage 104 may be a data/knowledge repository and/or a database that may be written and/or read by one or a combination of component 140, server computer 120 and computing device 110. In the depicted embodiment, shared storage 124 resides on server computer 120 and local storage 104 resides on computing device 110. In another embodiment, shared storage 124 and/or local storage 104 may reside elsewhere within distributed data processing environment 100, provided that each may access and is accessible by computing device 110 and server computer 120. Shared storage 124 and/or local storage 104 may each be implemented with any type of storage device capable of storing data and configuration files that may be accessed and utilized by server computer 120, such as, but not limited to, a database server, a hard disk drive, or a flash memory.

In some embodiments of the present invention, shared storage 124 and/or local storage 104 may each be a hard drive, a memory card, a computer output to laser disc (cold storage), and/or any form of data storage known in the art. In some embodiments, shared storage 124 and/or local storage 104 may each be one or more cloud storage systems and/or databases linked to a cloud network. In various embodiments, shared storage 124 and/or local storage 104 may access, store, and/or house user data, physical room data, and meeting data, and/or data shared throughout distributed data processing environment 100.

In the depicted embodiment, downsampling component (component) 140 is executed on server computer 120. In other embodiments, downsampling component 140 may be executed on computing device 110. In various embodiments of the present invention, not depicted in FIG. 1, downsampling component 140 may execute on a plurality of server computers 120 and/or on a plurality of computing devices 110. In some embodiments, component 140 may be located and/or executed anywhere within distributed data processing environment 100 as long as downsampling component 140 is connected to and/or communicates with computing device 110 and/or server computer 120, via network 130. In the depicted embodiment, encoder 142, decoder 144, and analytics engine 146 are each located and executed on downsampling component 140. In various embodiments, not depicted in FIG. 1, encoder 142, decoder 144, and analytics engine 146 may execute anywhere within distributed data processing environment 100 as long as encoder 142, decoder 144, and/or analytics engine 146 are each connected to and/or communicate with computing device 110 and/or server computer 120, via network 130.

In various embodiments of the present invention, encoder 142 may be one or more of: modified encoders, audio encoders, simple encoders, priority encoders, compressors, rotary encoders, linear encoders, absolute encoders, incremental encoders, and/or any type of encoder known in the art. In various embodiments of the present invention, decoder 144 may be one or more of: audio decoders, binary decoders, decompression decoders, instruction decoders, quadrature decoders, video decoders, and/or any other decoder known in the art. Analytics engine 146 may be one or more analytics engines as they are understood in the art.

In various embodiments, downsampling component 140, via encoder 142, utilizes a probabilistic resampling framework to select a subset of read fragments from an entire file. The encoder (e.g., encoder 142), performs optimization of bootstrapping to produce a set of resamples for a given N size (e.g., N=1 million reads that may have a total of 100 resamples). In various embodiments of the present invention, downsampling component 140, via encoder 142, selects a subset of encoded read fragments from one or more resamples after satisfying one or more predetermined criteria. In various embodiments of the present invention, decoder 144 may be used to produce a final set of read fragments that are representative of the original FASTQ file. In various embodiments of the present invention, decoder 144 is used to generate the final read fragments that may be placed in the final resample. In various embodiments of the present invention, decoder 144 may be used to produce x' (i.e. the final representative resample). Decoder 144 may reconstruct one or more of the vector representations that encode the reads as they move through the pipeline to generate the actual read/DNA fragments.

In various embodiments of the present invention, downsampling component 140 consists of two steps: first, an encoder (e.g., encoder 142) retrieves and/or receives genomic sequence data and performs bootstrapping to produce resamples, wherein unrepresentativeness and self-inconsistency of the produced resamples are assessed, where the variation is minimized, and wherein the most representative resample is selected; second, a decoder (e.g., decoder 144) receives as an input the most representative sample (e.g., the selected most representative resample) and produces a reconstruction of the original input reads. In various embodiments of the present invention, downsampling component 140 removes duplicate reads from a FASTQ file to reduce redundancy of genomic information. In various embodiments of the present invention, downsampling component 140 may process a FASTQ file containing millions and/or billions of reads by tagging one or more reads (e.g., all the reads) with a unique identifier and then mapping them to a sample reference sequence. In various embodiments of the present invention, downsampling component 140, via encoder 142, may encode positional information and mapping and quality scores for each read fragment. In various embodiments of the present invention, a statistical model is trained to estimate genotype likelihoods at each position and encode this information for each read fragment, via encoder 142.

In various embodiments of the present invention, downsampling component 140 may, without compromising (i.e., while maintaining) the genomic integrity of the original file, resample DNA fragments generated from massively parallel sequencing. For example, the genomic integrity refers to a genomic variation that results in different phenotypes and is encoded in different reads (i.e., a plurality or plethora of reads). In this particular example, in order to maintain the genomic integrity downsampling component 140 executes downsampling on one or more of the plurality of reads, wherein downsampling component 140 retains a majority or predetermined amounts of reads.

In various embodiments of the present invention, downsampling component 140, via encoder 142, may retrieve and/or receive genomic sequence data (e.g., DNA sequence data) from one or more users, one or more databases, and/or from one or more search engines and perform bootstrapping on the retrieve and/or receive genomic sequence data to produce resamples. In various embodiments of the present invention, downsampling component 140, via encoder 142, may perform probabilistic resampling to obtain a set of resamples containing a plurality of reads. In various embodiments of the present invention, component 140 may assess unrepresentativeness and self-inconsistency for resamples and selecting the best/"most representative" resample.

In various embodiments of the present invention, downsampling component 140, via encoder 142, may build representations from genotype likelihoods (e.g., transforming genomic reads that are in FASTQ format into a numerical vector representation). Downsampling component 140, via analytics engine 146, may integrate mapping positional information and genotype likelihoods to identify the optimum vector representation of a resample. In various embodiments of the present invention, downsampling component 140, via decoder 144, may retrieve and/or receive as an input the most representative sample and produces a reconstruction of the original input reads. In various embodiments of the present invention, downsampling component 140, via decoder 144, may decode the vector representation of the optimum resample to obtain a downsampled read file that resembles and maintains the genomic integrity of the original file.

In various embodiments of the present invention, given several reads overlapping a genomic location, the algorithm estimates genotype likelihood probabilities per read by maximizing the joint likelihood function parameters. These parameters are based on the Poisson Graphical Distribution (PGD). The likelihood of the parameters $\theta_0, \ldots, \theta_{D-1}$ is the probability that the read was sampled from a distribution with these particular parameters. This can be simplified in Equation 1 as follows:

$$L(\theta_1 \ldots \ldots \theta_n) = \prod_{i=1}^{N} \frac{e^{-\theta_{1n_1}}(\theta_1 n_1)^k}{k!}$$

$$\prod_{i=1}^{N} \frac{e^{-\theta_{2n_2}}(\theta_2 n_2)^k}{k!} \prod_{i=1}^{N} \frac{e^{-\theta_{3n_3}}(\theta_3 n_3)^k}{k!} \ldots \ldots \ldots \prod_{i=1}^{N} \frac{e^{-\theta_{nn_n}}(\theta_1 n_n)^k}{k!}$$

Equation 1

The test statistic may stay the same if the likelihood values are computed by pooling together genotype counts across multiple reads. For each read, a probability is estimated for each possible likelihood genotype.

In various embodiments of the present invention, resamples are generated using bootstrapping methods. For each bootstrapping iteration, given a FASTQ $X_N$ where X is the FASTQ file with N total number of reads, a portion of reads is randomly selected to produce $x_{1n}$, sampling with replacement (FIG. 2B). This process is repeated I number for times. In the next iteration of the resampling procedure $x_n$ is selected by increasing the number of reads.

To find the best $Z_i$ (i.e., Z where Z is the best set of resamples obtained from the bootstrapping), self-inconsistency and unrepresentativeness are applied where, Self-inconsistency is defined using Equation 2:

$$\mathcal{D}_{si}(N, K, N_r) = \frac{1}{N_r(N_r - 1)} \Sigma_{p \neq q} \forall_{p,q\{1,2 \ldots N_r\}}(D_{LK}(\theta_k(x_{ip}), \theta_k(x_{iq})))$$

Equation 2

The average over self-inconsistency is then taken using Equation 3:

$$\mathcal{D}_s(N, K) = \frac{1}{m} \Sigma_i \mathcal{D}_{si}(N, k, N_r)$$

Equation 3

Unrepresentativeness is defined using Equation 4:

$$\mathcal{D}_{ri}(N, K, N_r) = \frac{1}{N_r} \Sigma_{\forall p,q\{1,2 \ldots N_r\}}(D_{LK}(\theta_k(X_i), \theta_k(X_i)))$$

Equation 4

The average over self-inconsistency is then taken using Equation 5:

$$\mathcal{D}_r(N, K) = \frac{1}{m} \Sigma_i \mathcal{D}_{ri}(N, k, N_r)$$

Equation 5

It should be noted that in Equation 1 N represents the sample size (the number of reads in the original file), n represents the resample size (the number of reads in the resample), θ represents the Poison rate. It should be noted that in Equations 2-5 Nr represents the number of resamples, N represents the number of sequences/reads in each, K represents the k-mer size, M represents the total number of samples, $\mathcal{D}_{ri}$ represents unrepresentativeness, and $\mathcal{D}_s$ represents self-inconsistency. In various embodiments of the present invention, a set of resamples are selected to be further processed by analytics engine 146. In various embodiments of the present invention, the input into analytics engine 146 is a set of resamples (e.g. 100 resamples each containing 1 million reads (that is a selected set of 100 resamples, and each resample contains 1 million reads)). Analytics engine 146 may then process the 100 resamples to get the best resample that is truly representative of the original file. This is done by minimizing the steps in the equations as described below.

To get the best resample or set of resamples (i.e., optimal resample(s)), wherein the best resample or set of resamples are resample(s) with the lowest values of unrepresentativeness and self-inconsistency, positional information and genotype likelihoods are combined and analyzed as follows:

Given $Q_\theta$ ($\mathcal{Z}$ |X) where $\mathcal{Z}$ is the best set of resamples obtained from the bootstrapping and $z_i \ldots z_n$ are single resamples with m reads and X is the whole FASTQ file and $\mathcal{P}_\theta(X|[z, y])$, where y is the constraint obtained from alignment, which includes positional information of reads and their corresponding genotypic information minimize: $\mathcal{D}_{KL}[q_\theta([z, y]|X) \; \mathcal{P}_\theta(X|[z, y])]$ which implies $[z,y] \sim X$, such that $q_\theta([z, y]|X)$ at its minimum gives the best $[z,y]$ considering one or more constraints. In various embodiments of the present invention, the best $[z, y]$ is passed through decoder 144, which produces a down-sampled FASTQ file with a reduced number of reads, but the reads that are retained maintain the genomic integrity of the input file.

In other embodiments of the present invention, downsampling component 140 may further use one or more constraints to identify an optimal set of resamples (i.e., best Z). The one or more constraints that may be utilized by downsampling component 140 to identify an optimal set of resamples may comprise: (i) selecting the largest interval based on the positional information encoded from the mapping; (ii) calculating the distribution of the intervals in each resample such that positional coverage is maximized; (iii) finding a resample with minimum overlap that has the biggest coverage distribution; (iv) calculating the average read weight, based on the genotype likelihoods occurring on each read; and/or calculating the overall weight of the resample by considering the weights of the reads.

Figure 2A:
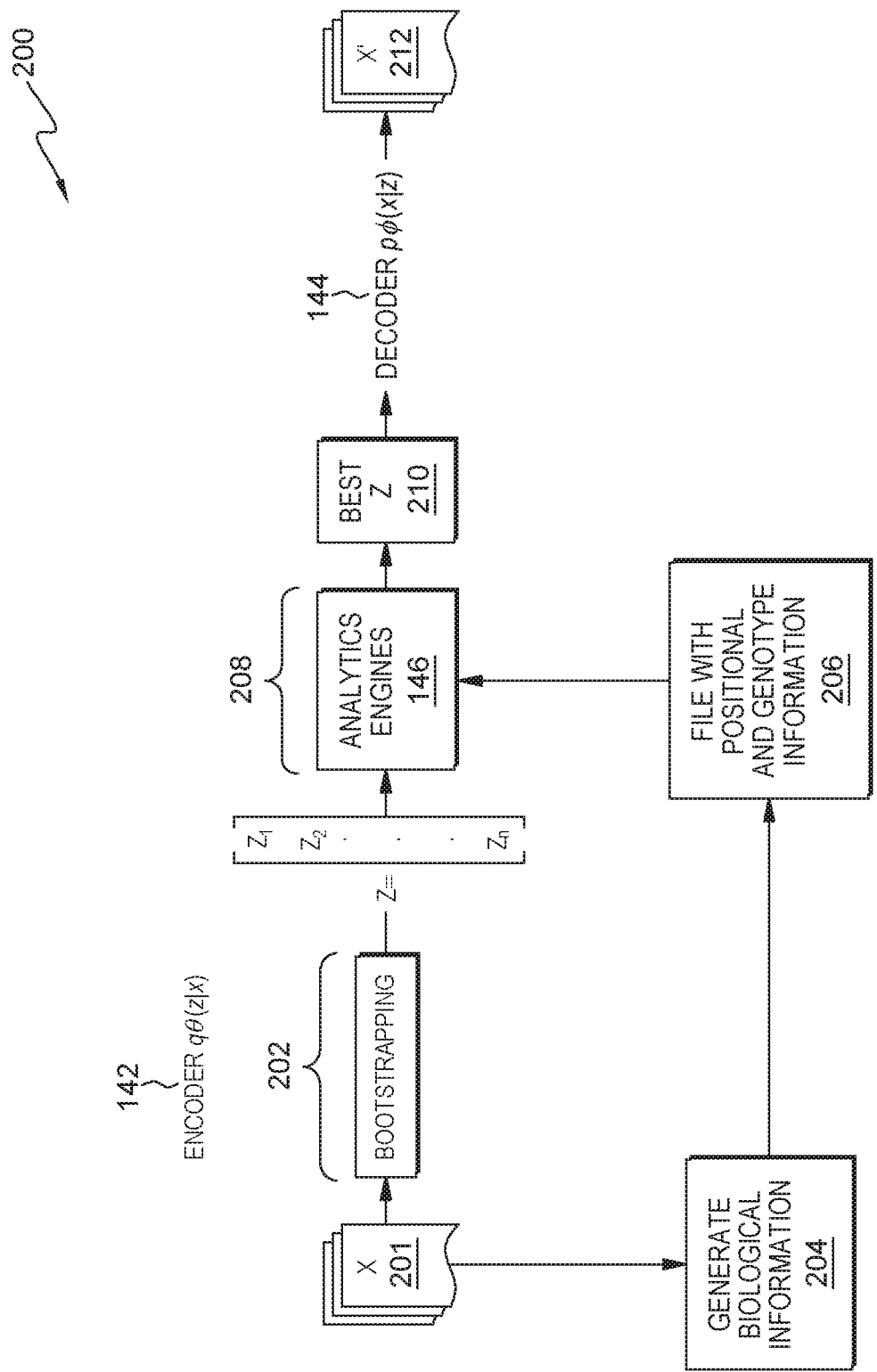
FIG. 2A illustrates a block diagram depicting a downsampling component, executing on a server computer, within distributed data processing environment of FIG. 1, for downsampling DNA sequence data using variational autoencoders, in accordance with an embodiment of the present invention.
Figure 2B:
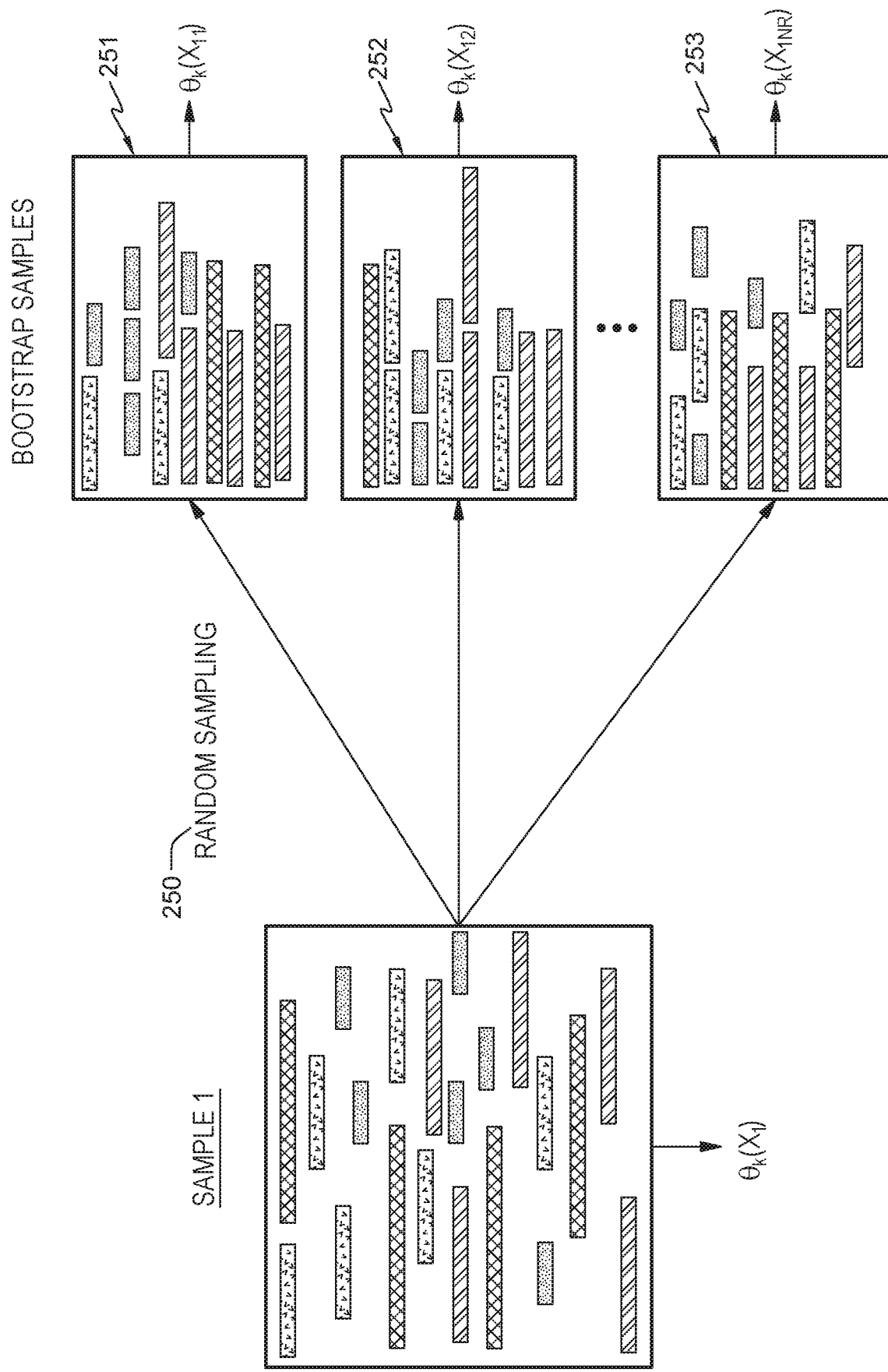
FIG. 2B is an example of the overview of the bootstrapping procedure, in accordance with an embodiment of the present invention.

FIG. 2A illustrates a block diagram depicting downsampling component 140 in communication with computing device 110 and/or server computer 120, within distributed data processing environment 100 of FIG. 1, for downsampling DNA sequence data using variational autoencoders. FIG. 2A provides one specific example of an overview of the steps followed to down-sample a FASTQ file using modified variational autoencoders. FIG. 2A provides an illustration of one implementation and does not imply any limitations with regard to the environments in which different embodiments may be implemented. Many modifications to the depicted environment may be made by those skilled in the art without departing from the scope of the invention as recited by the claims.

In step 201, downsampling component 140 receives and/or retrieves DNA sequence data. In various embodiments of the present invention, downsampling component 140 may receive and/or retrieve DNA sequence data from a database or as input from a user or another program.

In step 202, downsampling component 140 performs bootstrapping on the DNA sequence data. In various embodiments of the present invention, downsampling component 140, via encoder 142, performs bootstrapping on the received and/or retrieved DNA sequence data. In various embodiments of the present invention, downsampling component 140 uses a modified variational encoder (e.g., encoder 142) to perform probabilistic resampling to obtain a set of resamples containing a plurality of reads, depicted in FIG. 2B. The selected resamples may be self-consistent and representative of the original file, wherein self-consistency describes the minimum variation occurring among resamples of the same size for a given number of resampling iterations and representativeness is the minimization of resample variation with respect to the original file. In various embodiments of the present invention, downsampling component 140 ensures that its genomic integrity is maintained using Equations 2-5 (described above). To obtain a set of resamples that are self-consistent, downsampling component 140 compares the similarity in distribution of the samples, and in doing so, it uses hash tables in the encoder to perform the distributional computation.

For example, FIG. 2B, provides an example of the overview of the bootstrapping procedure. In FIG. 2B, sample 1, represented as $\theta_k(X_1)$, undergoes random sampling 250 and produces an amount 'n' of bootstrap sample, where 'n' is a predetermined amount. In this particular example, encoder 142 outputs bootstrap sample 251 represented as $\theta_k(X_{11})$, bootstrap sample 252 represented as $\theta_k(X_{12})$, and bootstrap sample 253 represented as $\theta_k(X_{1NR})$.

In step 204, downsampling component 140 generates biological information. In various embodiments of the present invention, downsampling component 140 generates biological information further described in FIG. 2C. Biological information may include positional information, genotype likelihood, and/or any other biological information known in the art.

In step 206, downsampling component 140 generates files with positional and genotype information. In various embodiments of the present invention, downsampling component 140 generates files with positional and genotype information further described in FIG. 2C.

In step 208, downsampling component 140 integrates mapping positional information and genotype likelihoods. In various embodiments, downsampling component 140, via analytics engine 146, may integrate mapping positional information and genotype likelihoods to identify the optimum vector representation of a resample. Analytics engine 146 calculates interval distribution for a plurality of reads in each resample such that nucleotide positional coverage is maximized and finds a plurality of reads in a resample with minimum overlap that has the biggest nucleotide coverage distribution for a given sample genome. Analytics engine 146 may also calculate the average read weight, based on a plurality of genotype likelihoods occurring on each read and overall weight of the resample based on the weights of a plurality of reads.

In step 210, downsampling component 140 can identify the best Z. In various embodiments of the present invention, downsampling component 140, via analytics engine 146, may identify the best Z. In various embodiments, downsampling component 140, via analytics engine 146, may calculate and display a list of the best Z's to a user.

In step 212, downsampling component 140 decodes the vector representation of an optimum resample. In various embodiments of the present invention, downsampling component 140, via decoder 144, may decode the vector representation of the optimum resample to obtain a downsampled read file that resembles and maintains the genomic integrity of the original file.

Figure 2C:
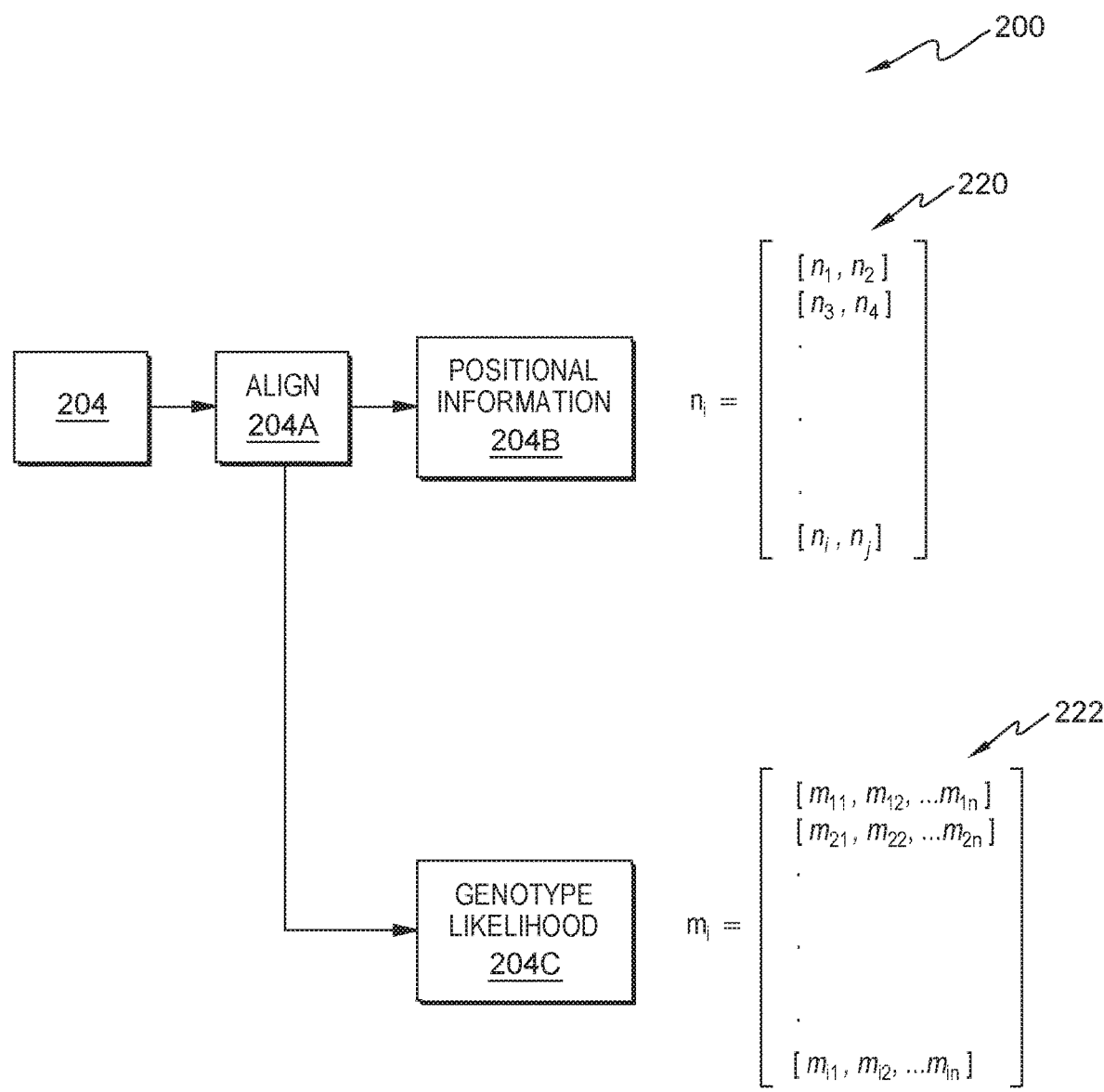
FIG. 2C illustrates a block diagram depicting an overview of biological information generation, within distributed data processing environment of FIG. 1, for downsampling DNA sequence data using variational autoencoders, in accordance with an embodiment of the present invention

FIG. 2C illustrates a block diagram depicting downsampling component 140 in communication with computing device 110 and/or server computer 120, within distributed data processing environment 100 of FIG. 1, for downsampling DNA sequence data using variational autoencoders. FIG. 2C provides an overview of biological information generation, wherein read fragments are mapped and the read fragment's positional information and genotype likelihoods are encoded into a numerical representation. FIG. 2C provides an illustration of one implementation and does not imply any limitations with regard to the environments in which different embodiments may be implemented. Many modifications to the depicted environment may be made by those skilled in the art without departing from the scope of the invention as recited by the claims.

In step 204, downsampling component 140 generates biological information. In various embodiments of the present invention, downsampling component 140 enables resampling DNA fragments generated from massively parallel sequencing, without compromising the genomic integrity of the original file.

In step 204A, downsampling component 140 aligns nucleotides. In various embodiments of the present invention, downsampling component 140 utilizes a modified variational encoder (e.g., encoder 142), where in encoder 142 aligns a plurality of reads containing nucleotides to different locations on a sample genome.

In step 204B downsampling component 140 generates positional information for the aligned plurality of reads. In various embodiments of the present invention, downsampling component 140, via encoder 142, may generate and/or identify positional information for the nucleotides in the aligned plurality of reads, wherein positional information comprises: mapping positions, mapping scores and nucleotide quality scores of a plurality of reads that map. In various embodiments of the present invention, downsampling component 140, via encoder 142, may encode mapping positions, mapping scores and nucleotide quality scores of a plurality of reads that map to a specific location of a sample genome into a vector representation. For example, a FASTQ file with millions of reads is mapped to a reference genome using the Smith-Waterman algorithm, as it is known in the art. The Smith-Waterman algorithm performs local sequence alignment to determine similar regions between two strings of nucleic acid sequences. The mapping position of each read is then encoded into a matrix as a start and end position (matrix 220). In matrix 220, the matrix structure comprises start and end positions of reads with data structure [n1, and n2] intervals continuously until the biological data and/or plurality of reads are represented, wherein n may be any positional, integer and/or numerical representation known in the art.

In step 204C, downsampling component 140 obtains genotype likelihoods for one or more genomic locations from the plurality of reads, wherein genotype likelihoods are a plurality of alleles with specified positional change on the plurality of reads. In various embodiments of the present invention, encoder 142 is modified to use the Poisson Graphical Distribution model (Equation 1) to obtain genotype likelihoods for each genomic location from a plurality of reads. In various embodiments of the present invention, downsampling component 140, via encoder 142, determines that a genotype likelihood matches a plurality of reads, where a genotype likelihood gives a probability of an allele occurring at a nucleotide position and discards low genotype likelihood probabilities that are not supported by a plurality of sequence reads.

In various embodiments of the present invention, a modified encoder (e.g., encoder 142) uses a plurality of genotype likelihoods on a read to calculate and determine read weight, down weighting reads with a few genotype likelihoods and discarding sequences without any genotype likelihoods estimated at any nucleotide position and sequences that do not map to any location on the sample genome to minimize redundancy. In various embodiments of the present invention, a modified encoder (e.g., encoder 142) may be used to build representations from genotype likelihoods. The representations capture the genomic nuances in the original file such that the genomic variation in the original file is maintained in the down-sampled representations.

To calculate genotype likelihoods on each read, positions of the reference genome are not considered independently, but rather in consort to ensure that accumulation of genotypes is taken into consideration at the read level. This enables positional read anomalies to be viewed as dependent instead of assuming independency. Assuming that the occurrences of reads overlapping positions where there is an accumulation of genotypes is random, the genotype likelihoods can be modelled using PGD. A PGD pulls together the count of reads overlapping a position taking into consideration their dependence.

In addition, PGDs treat reads overlapping a genomic position in relation to the reference as an exponential family of multinomial joint distributions. This enables modelling the dependencies between the count of reads overlapping a location assuming an upper bound, which is reasonable to make especially considering read depth. A joint likelihood function may estimate the likelihood genotype call as a probability of a change from the reference to the alternate allele. Reads overlapping a genotype location are encoded into a matrix (e.g., matrix 222) that is used to train a model for estimating genotype likelihood probabilities. The estimated genotype likelihood probabilities are also used for weighting reads. Thus, the majority of reads that have accumulated more genotype likelihoods ideally can be found in the same re-sample, ensuring that the genomic integrity of the original file is maintained. Resamples with higher than average accumulated genotype likelihoods are weighted upwards to increase their chance of selection.

Figure 3:
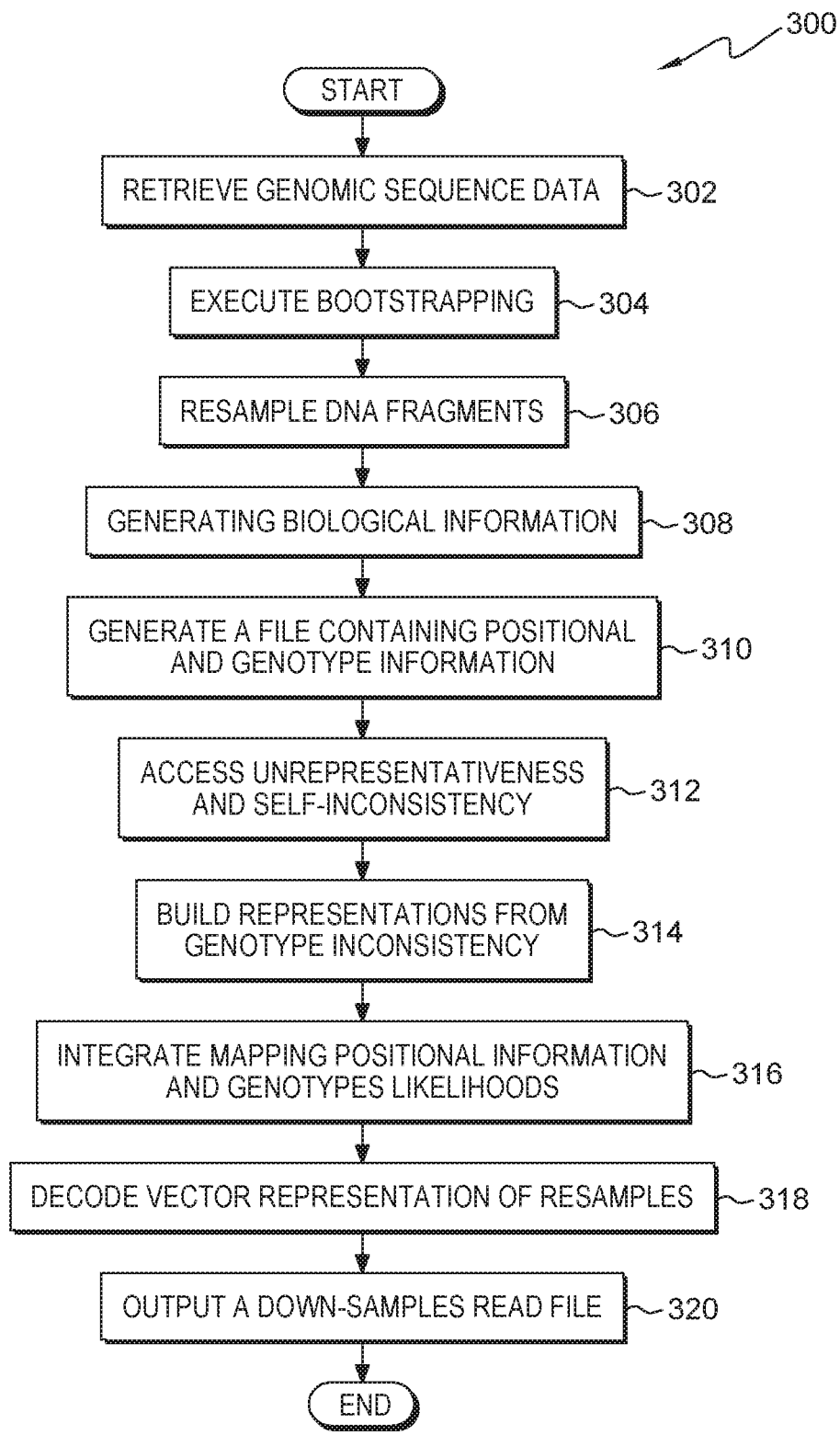
FIG. 3 illustrates operational steps of the downsampling component, on a computing device within the distributed data processing environment of FIG. 1, for automatically downsampling DNA sequence data using variational autoencoders, in accordance with an embodiment of the present invention.

FIG. 3 illustrates operational steps of downsampling component 140, generally designated 300, in communication with computing device 110, within distributed data processing environment 100 of FIG. 1, for automatically downsampling DNA sequence data using variational autoencoders, in accordance with an embodiment of the present invention. FIG. 3 provides an illustration of one implementation and does not imply any limitations with regard to the environments in which different embodiments may be implemented. Many modifications to the depicted environment may be made by those skilled in the art without departing from the scope of the invention as recited by the claims.

In step 302, downsampling component 140 retrieves genomic sequence data from a file. In various embodiments of the present invention, downsampling component 140 may retrieve and/or receive genomic sequence data from one or more files, one or more databases, one or more search engines, and/or manually input data.

In step 304, downsampling component 140 executes bootstrapping to produce resamples. In various embodiments of the present invention, downsampling component 140, via encoder 142, may perform bootstrapping on the received and/or retrieved genomic sequence data to produce resamples. In various embodiments of the present invention, downsampling component 140, via a modified variational encoder (e.g., encoder 142) may perform probabilistic resampling to obtain a ser of resamples containing a plurality of reads.

In step 306, downsampling component 140 resamples DNA fragments. In various embodiments of the present invention, downsampling component 140 may resample DNA fragments generated from parallel sequencing without compromising the genomic integrity of the original file.

In step 308, downsampling component 140 generates biological information. In various embodiments of the present invention, downsampling component 140, via encoder 142, may generate biological information wherein read fragments are mapped and the read fragment's positional information and genotype likelihoods are encoded into a numerical representation, as shown in FIG. 2C.

In step 310, downsampling component 140 generates a file containing positional and genotype information. In various embodiments of the present invention, downsampling component 140, via encoder 142, may generate one or more files containing positional and genotype information.

In step 312, downsampling component 140 accesses unrepresentativeness and self-inconsistency of the produced resamples. In various embodiments of the present invention, downsampling component 140, via encoder 142, may access the unrepresentativeness and self-inconsistency of one or more of the produced resamples and selecting one or more representative resample.

In step 314, downsampling component 140 builds representation from genotype likelihoods. In various embodiments of the present invention, downsampling component 140, via encoder 142 (e.g., a modified encoder), may build one or more vector representations from the genotype likelihoods.

In step 316, downsampling component 140 integrates mapping positional information and genotype likelihoods. In various embodiments of the present invention, downsampling component 140, via analytics engine 146, may integrate mapping positional information and genotype likelihoods to identify one or more optimum vector representations of one or more resamples.

In step 318, downsampling component 140 decodes vector representation of resamples. In various embodiments of the present invention, downsampling component 140, via decoder 144, may receive as input the representative sample and produce a reconstruction of the original input reads. In various embodiments of the present invention, downsampling component 140, via decoder 144 (e.g., a modified decoder), decode vector representation of the optimum resample to obtain a down-sampled read file that resembles and maintains the genomic integrity of the original file.

In step 320, downsampling component 140 outputs a down-sampled read file. In various embodiments of the present invention, downsampling component 140, via decoder 144, may output one or more down sample read files, that resembles and maintains the genomic integrity of the original file, to one or more users by displaying the data on UI 106 and/or displaying response prompts alerting the user of the file data. In various embodiments of the present invention, downsampling component 140, via decoder 144, may execute the one or more down sample read files, that resembles and maintains the genomic integrity of the original file.

Figure 4:
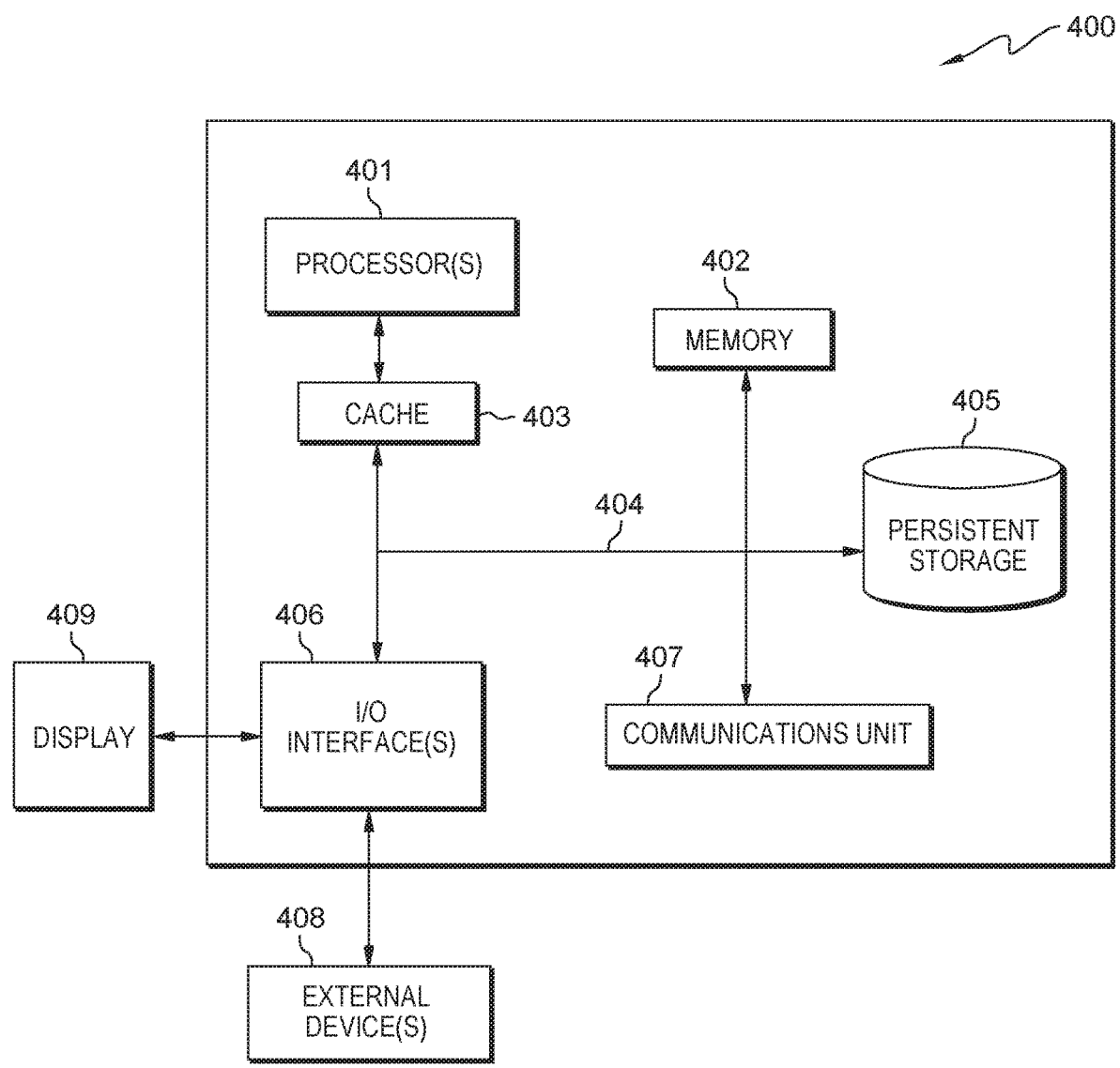
FIG. 4 depicts a block diagram of components of the server computer executing the downsampling component within the distributed data processing environment of FIG. 1, in accordance with an embodiment of the present invention.

FIG. 4 depicts a block diagram of components of server computer 120 within distributed data processing environment 100 of FIG. 1, in accordance with an embodiment of the present invention. It should be appreciated that FIG. 4 provides only an illustration of one implementation and does not imply any limitations with regard to the environments in which different embodiments may be implemented. Many modifications to the depicted environment may be made.

FIG. 4 depicts computer system 400, where server computing 120 represents an example of computer system 400 that includes downsampling component 140. The computer system includes processors 401, cache 403, memory 402, persistent storage 405, communications unit 407, input/output (I/O) interface(s) 406, display 409, external device(s) 408 and communications fabric 404. Communications fabric 404 provides communications between cache 403, memory 402, persistent storage 405, communications unit 407, and input/output (I/O) interface(s) 406. Communications fabric 404 may be implemented with any architecture designed for passing data and/or control information between processors (such as microprocessors, communications, and network processors, etc.), system memory, peripheral devices, and any other hardware components within a system. For example, communications fabric 404 may be implemented with one or more buses or a crossbar switch.

Memory 402 and persistent storage 405 are computer readable storage media. In this embodiment, memory 402 includes random access memory (RAM). In general, memory 402 may include any suitable volatile or non-volatile computer readable storage media. Cache 403 is a fast memory that enhances the performance of processors 401 by holding recently accessed data, and data near recently accessed data, from memory 402.

Program instructions and data used to practice embodiments of the present invention may be stored in persistent storage 405 and in memory 402 for execution by one or more of the respective processors 401 via cache 403. In an embodiment, persistent storage 405 includes a magnetic hard disk drive. Alternatively, or in addition to a magnetic hard disk drive, persistent storage 405 may include a solid-state hard drive, a semiconductor storage device, read-only memory (ROM), erasable programmable read-only memory (EPROM), flash memory, or any other computer readable storage media that is capable of storing program instructions or digital information.

The media used by persistent storage 405 may also be removable. For example, a removable hard drive may be used for persistent storage 405. Other examples include optical and magnetic disks, thumb drives, and smart cards that are inserted into a drive for transfer onto another computer readable storage medium that is also part of persistent storage 405.

Communications unit 407, in these examples, provides for communications with other data processing systems or devices. In these examples, communications unit 407 includes one or more network interface cards. Communications unit 407 may provide communications through the use of either or both physical and wireless communications links. Program instructions and data used to practice embodiments of the present invention may be downloaded to persistent storage 405 through communications unit 407.

I/O interface(s) 406 enables for input and output of data with other devices that may be connected to each computer system. For example, I/O interface 406 may provide a connection to external devices 408 such as a keyboard, keypad, a touch screen, and/or some other suitable input device. External devices 408 may also include portable computer readable storage media such as, for example, thumb drives, portable optical or magnetic disks, and memory cards. Software and data used to practice embodiments of the present invention may be stored on such portable computer readable storage media and may be loaded onto persistent storage 405 via I/O interface(s) 406. I/O interface(s) 406 also connect to display 409.

Display 409 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium may be any tangible device that may retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein may be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, may be implemented by computer readable program instructions.

These computer readable program instructions may be provided to a processor of a general purpose computer, a special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that may direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the FIG.s illustrate the architecture, functionality, and operation of possible implementations of systems, methods, and computer program products according to various embodiments of the present invention. In this regard, each block in the flowchart or block diagrams may represent a module, a segment, or a portion of instructions, which comprises one or more executable instructions for implementing the specified logical function(s). In some alternative implementations, the functions noted in the blocks may occur out of the order noted in the FIG.s For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, may be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer-implemented method for automatically downsampling DNA sequence data using variational autoencoders and preserving genomic integrity of an original FASTQ file, the method comprising:

processing the original FASTQ file by tagging one or more reads with a unique identifier and mapping the reads to a sample reference sequence;

executing, by an encoder, bootstrapping on genomic sequence data to produce resamples based on the original FASTQ file, wherein the encoder utilizes a probabilistic resampling framework to select a subset of reads from the original FASTQ file and performs optimization of bootstrapping to produce a set of resamples for a size;

assessing, by the encoder, unrepresentativeness and self-inconsistency of the resamples and selecting a representative resample according to the assessment;

building, by the encoder, a first vector representation from genotype likelihoods based on the selected representative resample;

generating by the encoder, biological information, wherein generating the biological information including mapping positional information and genotype likelihoods comprises:

aligning, by the encoder, a plurality of reads containing nucleotides to different locations on a sample genome;

generating, by the encoder, the mapping positional information for the nucleotides in the aligned plurality of reads, wherein the mapping positional information comprises: mapping positions, mapping scores and nucleotide quality scores of a plurality of reads that map; and encoding, by the encoder, the mapping positions, the mapping scores and the nucleotide quality scores of a plurality of reads that map to a specific location of the sample genome into a second vector representation;

integrating, by an analytics engine, mapping positional information and the genotype likelihoods to identify an optimum vector representation of a resample; and decoding, by a decoder, the identified optimum vector representation of the resample to obtain a down-sampled read file that resembles and maintains the genomic integrity of the original FASTQ file, wherein the decoder produces a final set of read fragments that are representative of the original FASTQ file, and wherein the decoder reconstructs the first vector representation that encodes the reads as they move through the pipeline to generate the down-sampled read file.

2. The computer-implemented method of claim 1 further comprising:
resampling, by the encoder, DNA fragments generated from massively parallel sequencing, without compromising the genomic integrity of the original FASTQ file.

3. The computer-implemented method of claim 1 further comprising:
executing, by a modified variational encoder, probabilistic resampling to obtain a second set of resamples containing a plurality of reads.

4. The computer-implemented method of claim 1 further comprising:
receiving, by the decoder, the representative resample as input; and producing, by the decoder, a reconstruction of a plurality of original input reads based on received representative resample.

5. The computer-implemented method of claim 1 further comprising:

outputting the down-sampled read file that resembles and maintains the genomic integrity of the original FASTQ file to a user.

6. The computer-implemented method of claim 1 further comprising:
generating, by the encoder, a file containing positional and genotype information.

7. The computer-implemented method of claim 1, wherein generating the biological information further comprises:
obtaining, by the encoder, genotype likelihoods for one or more genomic locations from the plurality of reads, wherein the genotype likelihoods are a plurality of alleles with specified positional change on the plurality of reads.

8. A computer program product for automatically down-sampling DNA sequence data using variational autoencoders and preserving genomic integrity of an original FASTQ file, the computer program product comprising:
one or more computer readable storage medium and program instructions stored on the one or more computer readable storage medium, the stored program instructions comprising:

program instructions to process the original FASTQ file by tagging one or more reads with a unique identifier and mapping the reads to a sample reference sequence;

program instructions to execute, by an encoder, bootstrapping on genomic sequence data to produce resamples based on the original FASTQ file, wherein the encoder utilizes a probabilistic resampling framework to select a subset of reads from the original FASTQ file and performs optimization of bootstrapping to produce a set of resamples for a size;

program instructions to assess, by the encoder, unrepresentativeness and self-inconsistency of the resamples and selecting a representative resample according to the assessment;

program instructions to build, by the encoder, a first vector representation from genotype likelihoods based on the selected representative resample;

program instructions to generate by the encoder, biological information, wherein generating the biological information including mapping positional information and genotype likelihoods comprises:

program instructions to align, by the encoder, a plurality of reads containing nucleotides to different locations on a sample genome;

program instructions to generate, by the encoder, the mapping positional information for the nucleotides in the aligned plurality of reads, wherein the mapping positional information comprises: mapping positions, mapping scores and nucleotide quality scores of a plurality of reads that map; and program instructions to encode, by the encoder, the mapping positions, the mapping scores and the nucleotide quality scores of a plurality of reads that map to a specific location of the sample genome into a second vector representation;

program instructions to integrate, by an analytics engine, mapping positional information and the genotype likelihoods to identify an optimum vector representation of a resample; and program instructions to decode, by a decoder, the identified optimum vector representation of the resample to obtain a down-sampled read file that resembles and maintains the genomic integrity of the original FASTQ file, wherein the decoder produces a final set of read fragments that are representative of the original FASTQ file, and wherein the decoder reconstructs the first vector representation that encodes the reads as they move through the pipeline to generate the down-sampled read file.

9. The computer program product of claim 8 further comprising:
program instructions to resample, by the encoder, DNA fragments generated from massively parallel sequencing, without compromising the genomic integrity of the original FASTQ file.

10. The computer program product of claim 8 further comprising:
program instructions to execute, by a modified variational encoder, probabilistic resampling to obtain a second set of resamples containing a plurality of reads.

11. The computer program product of claim 8 further comprising:
program instructions to receive, by the decoder, the representative resample as input; and
program instructions to produce, by the decoder, a reconstruction of a plurality of original input reads based on received representative resample.

12. The computer program product of claim 8 further comprising:
program instructions to output the down-sampled read file that resembles and maintains the genomic integrity of the original FASTQ file to a user.

13. The computer program product of claim 8 further comprising:
program instructions to generate, by the encoder, a file containing positional and genotype information.

14. The computer program product of claim 8, wherein generating the biological information further comprises:
program instructions to obtain, by the encoder, genotype likelihoods for one or more genomic locations from the plurality of reads, wherein the genotype likelihoods are a plurality of alleles with specified positional change on the plurality of reads.

15. A computer system for automatically downsampling DNA sequence data using variational autoencoders and preserving genomic integrity of an original FASTQ file, the computer system comprising:
one or more computer processors;
one or more computer readable storage medium;
program instructions stored on the one or more computer readable storage medium for execution by at least one of the one or more computer processors, the stored program instructions comprising:
program instructions to process the original FASTQ file by tagging one or more reads with a unique identifier and mapping the reads to a sample reference sequence;
program instructions to execute, by an encoder, bootstrapping on genomic sequence data to produce resamples based on the original FASTQ file, wherein the encoder utilizes a probabilistic resampling framework to select a subset of reads from the original FASTQ file and performs optimization of bootstrapping to produce a set of resamples for a size;
program instructions to assess, by the encoder, unrepresentativeness and self-inconsistency of the resamples and selecting a representative resample according to the assessment;
program instructions to build, by the encoder, a first vector representation from genotype likelihoods based on the selected representative resample;
program instructions to generate by the encoder, biological information, wherein generating the biological information including mapping positional information and genotype likelihoods comprises:
program instructions to align, by the encoder, a plurality of reads containing nucleotides to different locations on a sample genome;
program instructions to generate, by the encoder, the mapping positional information for the nucleotides in the aligned plurality of reads, wherein the mapping positional information comprises: mapping positions, mapping scores and nucleotide quality scores of a plurality of reads that map; and
program instructions to encode, by the encoder, the mapping positions, the mapping scores and the nucleotide quality scores of a plurality of reads that map to a specific location of the sample genome into a second vector representation;
program instructions to integrate, by an analytics engine, mapping positional information and the genotype likelihoods to identify an optimum vector representation of a resample; and
program instructions to decode, by a decoder, the identified optimum vector representation of the resample to obtain a down-sampled read file that resembles and maintains the genomic integrity of the original FASTQ file, wherein the decoder produces a final set of read fragments that are representative of the original FASTQ file, and wherein the decoder reconstructs the first vector representation that encodes the reads as they move through the pipeline to generate the down-sampled read file.

16. The computer system of claim 15 further comprising:
program instructions to resample, by the encoder, DNA fragments generated from massively parallel sequencing, without compromising the genomic integrity of the original FASTQ file.

17. The computer system of claim 15 further comprising:
program instructions to execute, by a modified variational encoder, probabilistic resampling to obtain a second set of resamples containing a plurality of reads.

18. The computer system of claim 15 further comprising:
program instructions to receive, by the decoder, the representative resample as input; and
program instructions to produce, by the decoder, a reconstruction of a plurality of original input reads based on received representative resample.

19. The computer system of claim 15 further comprising:
program instructions to output the down-sampled read file that resembles and maintains the genomic integrity of the original FASTQ file to a user; and
program instructions to generate, by the encoder, a file containing positional and genotype information.

20. The computer system of claim 15, wherein generating the biological information further comprises:
program instructions to obtain, by the encoder, genotype likelihoods for one or more genomic locations from the plurality of reads, wherein the genotype likelihoods are a plurality of alleles with specified positional change on the plurality of reads.

* * * * *